(12) United States Patent
Akiba

(10) Patent No.: US 6,315,714 B1
(45) Date of Patent: Nov. 13, 2001

(54) ENDOSCOPE INSERTION GUIDE PIPE

(75) Inventor: Haruo Akiba, Omiya (JP)

(73) Assignee: Fuji Photo Optical Co., Ltd., Saitama (JP)

( * ) Notice: Subject to any disclaimer, the term of this patent is extended or adjusted under 35 U.S.C. 154(b) by 0 days.

(21) Appl. No.: 09/449,560

(22) Filed: Nov. 29, 1999

(30) Foreign Application Priority Data

Nov. 30, 1998 (JP) .................................................. 10-338901

(51) Int. Cl.$^7$ ...................................................... A61B 1/04
(52) U.S. Cl. ........................ 600/114; 600/129; 600/138; 604/524
(58) Field of Search .................................. 600/102, 114, 600/128, 129, 138; 604/524, 264

(56) References Cited

U.S. PATENT DOCUMENTS

| 3,805,770 | * | 4/1974 | Okada ........................................ 128/4 |
| 5,280,781 | * | 1/1994 | Oku ........................................... 128/4 |
| 5,337,733 | * | 8/1994 | Bauerfeind et al. ....................... 128/4 |
| 5,643,174 | * | 7/1997 | Yamamoto et al. .................. 600/114 |
| 5,941,815 | * | 4/1999 | Chang .................................... 600/114 |

FOREIGN PATENT DOCUMENTS 10248799    9/1998 (JP) .

* cited by examiner

Primary Examiner—Linda C. M. Dvorak
Assistant Examiner—Jocelyn Ram
(74) Attorney, Agent, or Firm—Snider & Associates; Ronald R. Snider

(57) ABSTRACT

A guide tube which stabilizes a guide position of a scope inserted into an object to be observed and serves to prevent a surface wall portion of the object to be observed from being pinched by a leading end. A metal ring and a hard plastic ring having a ring like convex portion are attached to a leading end of a main tube of the guide tube. The ring like convex portion is made, for example, of an elastic polyurethane resin and a protruding end has an inside diameter D1 which is slightly smaller than an outside diameter of a scope to be guided. The guide tube is capable of bringing the scope into close contact with an inside of the convex portion. Furthermore, the metal ring makes it possible to confirm a location of the guide tube by x-ray radioscopy inspection.

3 Claims, 4 Drawing Sheets

ENDOSCOPE INSERTION GUIDE PIPE

BACKGROUND OF THE INVENTION

This application claims the priority of Japanese Patent Application No. 10-338901 filed on Nov. 30, 1998, which is incorporated therein by reference.

1. Field of the Invention

The present invention relates to an endoscope insertion guide tube, and more specifically a configuration of a leading end of a guide tube which is used to insert a scope for digestive organs into a body to be observed.

2. Description of the Prior Art

For insertion of an endoscope (scope) for digestive organs into a body to be observed (for example a scope for small intestine), it is conventional to use a guide tube to aid insertion by maintaining straight an otherwise meandering insertion path of the digestive organs.

A condition of a guide tube which is in a condition disposed in digestive organs is shown in FIGS. 4(A) and 4(B), wherein a guide tube 1 is passed from a stomach 2 to a duodenum 3 and a scope 4 is led to the duodenum 3 or a small intestine under the duodenum while being guided by the guide tube 1, for example, as shown in FIG. 4(A). The guide tube 1 facilitates insertion of the scope 4.

However, the conventional guide pipe 1 allows a gap S to remain between the guide tube 1 and the scope 4 as shown in FIG. 4(B), thereby posing a problem that the scope 4 slightly moves (rattles) in the guide pipe 1 in a diametrical direction and is not stable in its position. Furthermore, a leading end port of the guide tube 1 may be slightly opened by a bending or the like of the scope 4, whereby a surface wall portion 5 of a body to be observed may be pinched in the gap S when the scope 4 is inserted or withdrawn. The gap S of a certain degree is necessary to smooth insertion of the scope 4 and cannot be eliminated completely.

Furthermore, there is available a conventional guide tube such as one disclosed by Japanese Patent Laid-Open No. 10-248799 using an auxiliary tube which is made of a flexible material and has a bulb portion having a circular sectional shape at a leading end so that the spherical portion is brought into close contact with an outer circumference of a scope. However, such an auxiliary tube which has flexibility allows the leading end to be deformed, thereby making it difficult to insert the scope or the auxiliary tube into a digestive organ.

FIGS. 5(A) and 5(B) show a condition of a guide tube which is deformed as described above, wherein a leading end of the guide tube 1 is inserted into a body and deformed into an elliptic shape as shown in FIG. 5(A) under an internal pressure, thereby making it hard to pass the scope 4 through a bulb portion 6 of the leading end. Furthermore, the guide tube 1 cannot hardly be moved for insertion of withdrawal along the scope 4 which as been inserted.

BRIEF SUMMARY OF THE INVENTION

The present invention which has been achieved in view of the problems described above has an object to provide an endoscope insertion guide tube which stabilizes a guide position for a scope, cannot pinch a surface wall portion of an object to be observed into a leading end port, and is free from deformation of the leading end port which degrades an insertion property of the scope and hinders smooth insertion and withdrawal of the guide tube.

In order to attain the object described above, an endoscope insertion guide tube as claimed in claim 1 is characterized by comprising: a main pipe which serves to guide an endoscope into a body to be observed; a hard ring which is disposed at a leading end of the man pipe and serves to prevent a leading end port from being deformed; and a ring like elastic convex member which is disposed in the leading end port, protrudes from an inside wall toward an axial center of the tube and has a protruding end having a diameter slightly smaller than an outside diameter of the endoscope.

An invention as claimed in claim 2 is characterized in that a metal ring whose position can be confirmed by X-ray silhouette inspection is disposed outside the ring like convex member disposed in the leading end port described above.

An invention as claimed in claim 3 is characterized by comprising: a main pipe which guides an endoscope into a body to be observed; a hard ring which is disposed in a leading end of the main pipe and serves to prevent a leading end port of the main pipe from being deformed; a metal ring which is integrated with the hard ring and has a size to be fitted inside the leading end of the main pipe and whose position can be confirmed by the X-ray silhouette inspection, a ring like elastic convex member which is disposed inside the metal ring and the hard ring, protrudes from an inside wall toward an axial center of the tube and has a protruding end having a diameter slightly smaller than an outside diameter of said endoscope; and a string which fixes the hard ring by binding an outer circumference of the main pipe to which the hard ring is attached together with the metal ring fitted therein.

The configuration described above brings an outer circumference of a scope into close contact with the ring like convex member in the elastic leading end port, thereby stabilizing a guide portion for the scope and preventing an inside wall portion of a digestive organ or the like from being pinched. Furthermore, the leading end port which is not deformed even under a pressure at an insertion time smoothes insertion of the scope as well as insertion and withdrawal of the guide tube.

Moreover, the metal ring makes it possible to easily confirm a position of the leading end port of the guide tube by the X-ray silhouette inspection when the metal ring is disposed in the leading end port.

DETAILED DESCRIPTION OF THE PREFERRED EMBODIMENTS

Figure 2A:
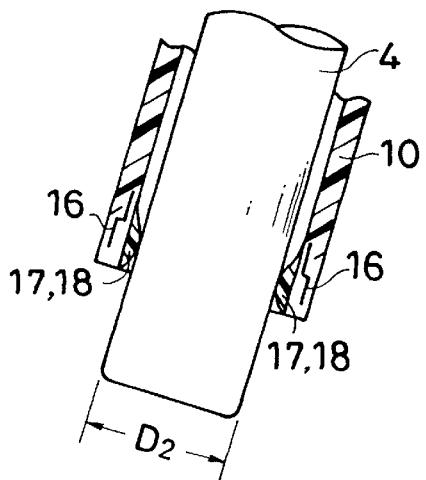
FIG. 2(A) is a partial sectional view showing a condition wherein a scope is inserted into the guide tube preferred as the embodiment.
Figure 2B:
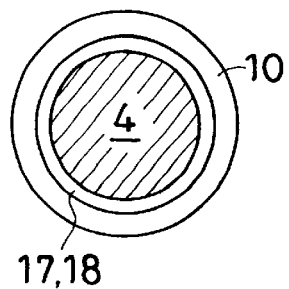
FIG. 2(B) is a leading end view of the scope shown in FIG. 2(A)
Figure 3:
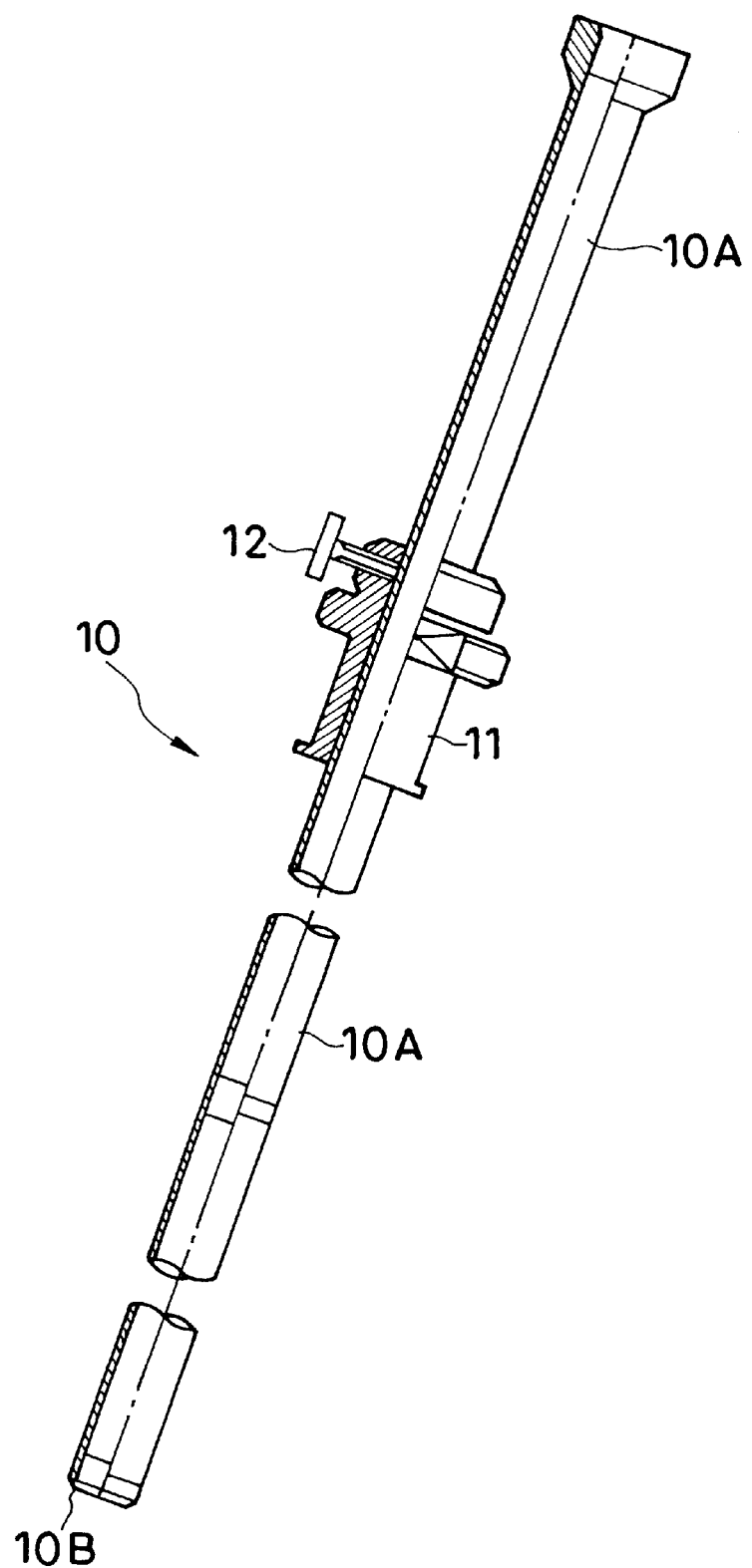
FIG. 3 a view (half sectional view) showing an overall configuration of the guide tube preferred as the embodiment.
Figure 4A:
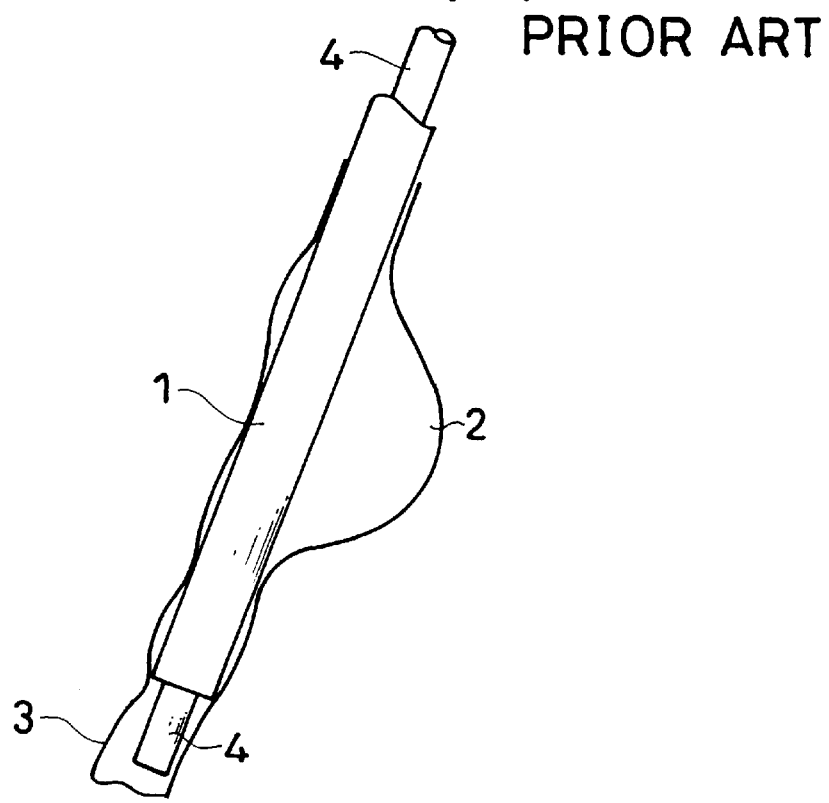
FIG. 4(A) a view descriptive of a condition where a scope is inserted into a conventional guide tube.
Figure 4B:
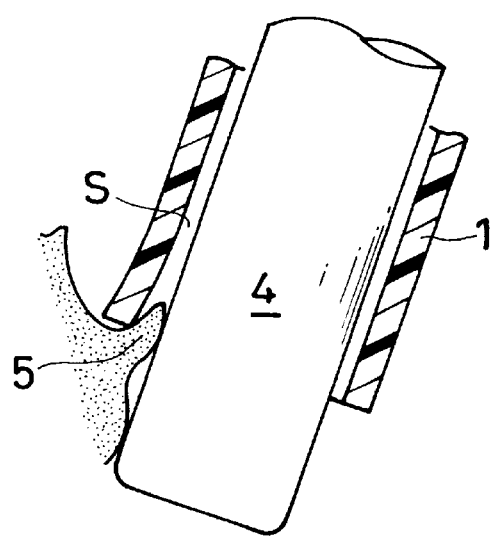
FIG. 4(B) is an enlarged view showing a leading end of the guide tube shown in FIG. 4(A)
Figure 5A:
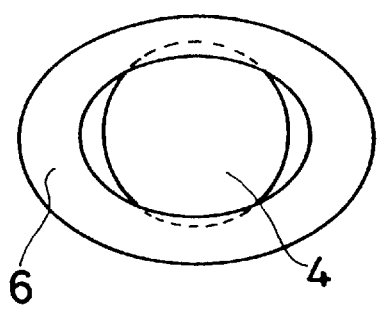
FIG. 5(A) is a leading end view showing a condition where a scope is inserted into another conventional guide tube.
Figure 5B:
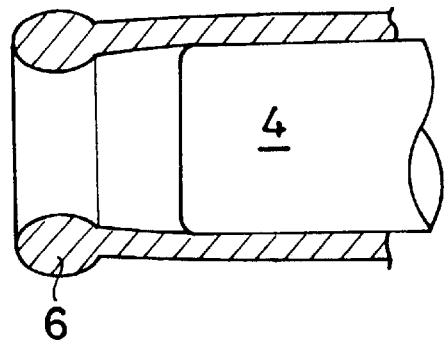
FIG. 5(B) is a partial sectional view of the guide tube shown in FIG. 5(A) as seen from its side.

FIGS. 1(A) through 3 show a configuration of an endoscope insertion guide tube preferred as an embodiment of the present invention. FIG. 3 shows a guide tube 10 preferred as the embodiment comprising a main tube 10A which is made, for example, of fluororubber in a form of a follow tube and a mouthpiece member 11 which is slidably disposed on an upper outer circumferential portion of the guide tube 10. A thread fixing type fixing knob 12 is disposed above the mouthpiece member 11. Accordingly, the mouthpiece member 11 can be fixed at an optional location on the guide tube 10 with the fixing knob 12.

Figure 1A:
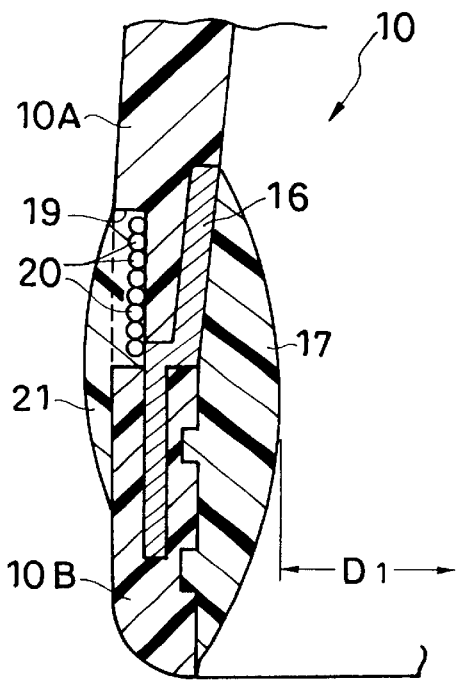
FIG. 1(A) is a sectional view showing a leading end piece portion of an endoscope insertion guide tube preferred as an embodiment of the present invention.
Figure 1B:
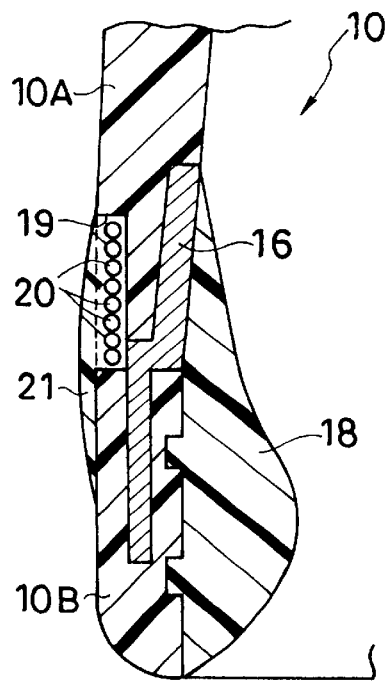
FIG. 1(B) is a sectional view showing a modification example of a ring like convex member of the guide tube.

FIGS. 1(A) and 1(B) show a configuration of a leading end port of the guide tube 10, wherein a hard plastic ring 10B is attached to a leading end of the main tube 10A as shown in FIG. 1(A). Speaking more concretely, a portion of a metal ring 16 which has a step is embedded into the plastic ring 10B and the metal ring 16 is formed in a size to be fitted inside the main tube 10A. Furthermore, attached inside these members is a ring like convex member 17 by bonding or the like. This ring like convex member 17 is made of an elastic material, for example an elastic polyurethane resin (or another synthetic resin material), and formed so as to have a protruding end having an inside diameter D1 of the protruding end of convex member 17 slightly smaller than an outside diameter D2 of a scope 4 to be guided (FIG. 2). The ring like convex member may have a form like that of a convex member 18 shown in FIG. 1(B).

After the plastic ring 10B to which the metal ring 16 and the convex member 17 are attached is connected to a leading end of the main tube 10A, the main tube 10A is bound with a thread 20 utilizing an outer circumferential groove 19 and a bound portion is fixed with an adhesive agent 21.

The guide tube 10 which has the configuration of the embodiment described above is inserted from a mouth straight into an intestine portion via a gullet and a stomach as described with reference to FIG. 3, end the metal ring 16 which is used in the embodiment makes it possible to easily confirm a position of the leading end port of the guide tube 10. Since inspections and surgical operations with an endoscope which utilizes the guide tube 10 are mostly conducted under x-ray silhouette inspections, the metal ring 16 permits confirming the position of the leading end of the guide tube 10, thereby making it possible to insert and locate the guide tube 10 without fail.

A condition of the scope 4 which is inserted in the guide tube 10 is shown in FIGS. 2(A) and 2(B), wherein the scope 4 is led out of the leading end port while the scope 4 is slightly expanding the ring like convex member 17, 18. Accordingly, the scope 4 is kept in close contact with the ring like convex member 17, whereby the scope 4 is not allowed to swing in the guide tube 10, and can be inserted and operated stably. Moreover, the guide tube 10 allows no gap to be formed between the guide tube and the scope 4 in the leading end port, thereby preventing a surface wall portion of a body to be observed from being pinched.

Since the embodiment adopts not only the ring like convex member 17 but also the hard plastic ring 10B attached to the leading end and the embedded metal ring 16, the embodiment prevents the leading end port of the guide 10 from being opened by an insertion pressure of the scope 4 or expanding force of a bending of the scope 4, thereby providing an effect to prevent the surface wall portion of the body to be observed from being pinched.

Furthermore, the leading end port of the guide tube 10 which is not deformed by an internal pressure of the body improves an insertion property of the scope 4, and assures smooth movements of the guide tube 10 along the inserted scope 4 for insertion and withdrawal of the guide tube 10.

As understood from the foregoing description, the embodiment described above stabilizes the guide position for the scope 4 and prevents the surface wall portion of the body to be observed from being pinched in the leading end port. The hard ring 10B prevents the leading end port from being deformed, thereby smoothing the insertion and withdrawal of the guide tube 10. Furthermore, the embodiment has an advantage that a position of the guide tube tip can be confirmed by the X-ray silhouette inspection, thereby inserting and locating the guide tube 10 and the scope 4 securely and easily.

What is claimed is:

1. An endoscope insertion guide tube comprising:
    a main tube which guides an endoscope into a body to be observed;
    a ring which is at a leading end of the main tube forming a leading end port and preventing the leading end port from being deformed; and
    an elastic convex ring member which is disposed in the leading end port, protrudes from an inside wall of the ring toward an axial center of the tube and has a protruding end having a diameter slightly smaller than an outside diameter of an endoscope to be inserted into the guide.

2. The endoscope insertion guide tube according to claim 1, wherein a metal ring whose location can be confirmed by X-ray silhouette inspection is disposed outside said convex ring member.

3. An endoscope insertion guide tube comprising:
    a main tube which guides an endoscope into a body to be observed;
    a ring which is at a leading end of the main tube, forming a leading end port and preventing the leading end port from being deformed;
    a metal ring which is formed integrally with the ring wherein the metal ring fits on the leading end of said main tube and whose location can be confirmed by X-ray silhouette inspection;
    an elastic convex ring which is disposed inside the metal ring and the hard ring, which protrudes from an inside wall of the ring disposed at a leading edge toward an axial center of the tube and which has an inner surface having a diameter slightly smaller than an outside diameter of an endoscope to be inserted into the guide; and
    a thread which is used to bind an outer circumference of said main tube to said ring.

* * * * *